United States Patent

Schranz et al.

[11] 3,993,809
[45] Nov. 23, 1976

[54] METHOD OF MEASURING A TWO-DIMENSIONAL TEMPERATURE DISTRIBUTION

[75] Inventors: Karl-Wilhelm Schranz, Odenthal-Hahnenberg; Wolfgang Hunicke, Leverkusen; Hildegard Schnoring, Wuppertal, all of Germany

[73] Assignee: AGFA-Gevaert, A.G., Leverkusen, Germany

[22] Filed: Mar. 6, 1975

[21] Appl. No.: 556,151

[30] Foreign Application Priority Data

Mar. 12, 1974 Germany............................ 2411767

[52] U.S. Cl.................................. 428/1; 73/355 R; 73/356; 128/2 H; 128/2.1 R; 428/40; 428/352
[51] Int. Cl.².......................................... C09K 3/34
[58] Field of Search........................ 428/1, 352, 40; 167/84.5; 128/2.1, 2; 73/355, 356; 350/160 LC

[56] References Cited
UNITED STATES PATENTS

| | | | |
|---|---|---|---|
| 2,524,286 | 10/1950 | Dreyer | 88/65 |
| 3,533,399 | 10/1970 | Goldberg | 128/2 |
| 3,852,092 | 12/1974 | Patterson | 428/1 |

*Primary Examiner*—Marion E. McCamish
*Attorney, Agent, or Firm*—Connolly and Hutz

[57] ABSTRACT

For measuring a two-dimensional temperature distribution a thermographic film is used which consists of a layer containing temperature-sensitive liquid crystals and an antireflection layer. The film is arranged an auxiliary support which is removed from the film before measurement. Only small layer adhesion forces prevail between the thermographic film and auxiliary support.

12 Claims, 5 Drawing Figures

METHOD OF MEASURING A TWO-DIMENSIONAL TEMPERATURE DISTRIBUTION

This invention relates to a method of measuring a two-dimensional temperature distribution using a thermographic film containing temperature-sensitive liquid crystals.

The identification of malignant tumours, blocked blood vessels or other disorders causing thermal anomalies by thermographic methods, is acquiring increasing significance in modern medicine.

In addition to infrared radiation measuring techniques, the esters of cholesterol which are known as "liquid crystals" are particularly suitable for thermographic temperature measurement. The properties of compounds of this class are described in detail in the literature, for example in Chemiker Zeitung 95, No. 15/16, pages 661 et seq (1971)

In addition, the structure and production of film systems containing a layer of liquid crystals are known to be important factors in practical temperature measurement (for example Peterson, Dixon — Obstetrics and Gynaecology, 37, 468 (1971) and Lauriente, Ferguson — Electronic Design, 15, ((1957).

It is important that the background of the layer of liquid crystals should be dark in color, preferably black. Otherwise the color density of the liquid crystals is reduced through reflection of the incident light by the background. Thus, the liquid crystals completely lose their play of colors where the background is pure white. In general, a temperature-measuring film (thermographic film) contains a temperature-sensitive liquid crystal layer, a black-colored layer (anti-reflection layer) and a supporting film. The supporting film can be arranged between the layer of liquid crystals and the black layer or before the layer of liquid crystals or behind the black layer. In the first two cases, the supporting film has to be transparent and colorless. The black layer/supporting film combination can also be replaced by a black-pigmented supporting film. Since the liquid crystals are extremely sensitive both to impurities and to oxidation, it is in some cases recommended to cover the layer of liquid crystals with another film.

In practice, the liquid crystals are protected against impurities by microencapsulation, the capsules containing a liquid crystal core and a shell of a binder impenetrable to impurities, for example of gelatin and/or gum arabic.

In order, in medicinal applications, to be able accurately to localize extremely fine differences in temperature, generally less than 0.5° C., the film used must supply extremely sharp thermographs. In German Offenlegungsschrift No. 2,152,277 a process is proposed for the production of a thermographie plate in which the layer containing temperature-sensitive liquid crystals is associated with a latex-based heat-conducting layer with a lattice effect perpendicular to the temperature-sensitive layer. The lattice effect is said to be produced by crosslinking a single latex layer at a temperature of 150° C or by depositing a number of extremely thin latex layers each with a thickness of less than 0.05 mm.

On the one hand, the proposed process involves considerable expense, with a result that plates of this kind are extremely expensive to manufacture. On the other hand, the corresponding thermographic plates have a number of disadvantages. The lattice effect acting perpendicular to the layer of liquid crystals is largely neutralized by the insulating effect of the supporting film, irrespective of whether the supporting film is situated in front of the anti-reflection layer, between the anti-reflection layer and the liquid crystal layer or behind the liquid crystal layer, looking in the direction of heat diffusion. When the plate is applied to parts of the skin, heat accumulates in the skin tissue which results in undesirable propagation of the heat zones and, hence, is blurred thermographs.

On the other hand, when placed on body tissue, especially in examinations for breast cancer, the support layer present in conventional thermographic films, consisting for example of a polyethylene glycol terephthalate film, gives rise to considerable deformation of the object under examination on account of its inelasticity, with the result that it is extremely difficult to localize the temperature anomaly with any degree of accuracy. In the absence of the support layer, the heat-conductive latex layer can only be used in relatively thick layers because the layer shows only limited strength either on account of the crosslinking of the molecules substantially perpendicular to the temperature-sensitive layer, or on account of the complete absence of crosslinking. When used in relatively thick layers, however, the heat-conductive latex layer loses its effect. In conjunction with an elastic supporting film, the latex layer easily tears if the film system is stretched.

The quality of the thermograph is terms of definition and resolving power is obviously governed to a very considerable extent by the thickness of the film. Thick film systems produce extremely blurred thermographs because, in the film, the conduction of heat in the direction of the layer (transverse conduction) takes on considerable proportions.

With decreasing layer thicknesses, the transverse conduction of heat is increasingly suppressed, with the result that the definition of the thermograph is increased.

The reduction in layer thickness is limited essentially by three factors, namely
  a. in the case of the temperature-sensitive, liquid crystal layer, by the reduction in the color densities attributable to the decrease in the packing density of the micro-capsules per unit area,
  b. in the case of the anti-reflection layer by the reduction in density (blackness),
  c. by the reduction in the mechanical strength of the film system.

However, it has been found that the layer thicknesses required for useful color saturation in the case of the liquid crystal layer are to a considerable extent governed by the capsule diameter of the microcapsules. Smaller capsules provide for thinner layers with the same color saturation. With the currently available microencapsulated liquid crystals, it is possible to form layers approximately 0.02 mm thick which still show adequate color saturation. With extremely fine dispersion of carbon black, it is possible to form useful anti-reflection layers approximately 0.005 mm thick. However, temperature-sensitive films with a layer thickness of the order of 0.025 mm cannot in practice economically be produced and handled, especially if the need for high elasticity in the film system is to be satisfied.

An object of the present invention is to provide a thermographic measuring technique using a thermographic film containing liquid crystals which is intended to show elastic properties for optimum adaptation to an object to be examined and which, in addition, is intended to be as thin as possible in order to enable the heat distribution to be recorded to be reproduced as accurately as possible. In addition, the thermographic film is of course intended to be easy to produce.

According to the invention, this object is achieved by using a layer combination in which the important layers of the thermographic film, namely the liquid crystal layer and the anti-reflection layer, are arranged on a temporary auxiliary substrate which is removed before the actual measurement.

Accordingly, the invention relates to a method of measuring a two-dimensional temperature distribution using a thermographic film containing temperature-sensitive liquid crystals. The method according to the invention is distinguished by the fact that a layer combination is used which comprises a thermographic film, arranged on an auxiliary substrate, a layer containing temperature-sensitive liquid crystals and an anti-reflection layer, the layer adhesion forces prevailing between the auxiliary substrate and the thermographic film being minimal, and by the fact that the auxiliary substrate is removed from the thermographic film before temperature measurement.

The invention also relates to a thermographic layer combination suitable for carrying out the method described above, which, on a substantially inelastic support layer (auxiliary substrate), carries a thermographic film which, in known manner, contains a temperature-sensitive liquid crystal layer and an anti-reflection layer by which, on account of its own particular elasticity properties, if removed from the auxiliary substrate causes only slight deformation of the object under examination during the actual measurement, and makes it possible for the temperature distribution to be measured to be reproduced accurately because of its limited layer thickness.

In the context of the invention, a two-dimensional temperature distribution is a temperature distribution within a surface. This surface can also be curved and, for example where the thermographic film according to the invention is used for medical diagnosis, is the surface, for example the skin, of a part of the body to be examined. From the temperature distribution in the surface, it is possible to draw conclusions as to processes or conditions within the space defined by the surface, for example within the body tissue under that part of the skin on which the measurement is being made.

The arrangement of the thermographic film on a temporary auxiliary substrate which is removed before the measurement affords significant advantages not only in terms of production but also in terms of application. The production of the thin, highly elastic film is simple and free from problems, because on the one hand, there are enough processes available for coating the auxiliary substrate, and because on the other hand the mechanical stressing applied during the processes following coating, for example drying, transport and storage is almost completely absorbed by the auxiliary substrate.

Further advantages will become apparent from the following description. The invention is illustrated by the embodiments of the thermographic layer combination shown on a greatly enlarged scale in FIGS. 1 to 5 of the accompanying drawings.

FIGS. 1 to 3 each show one embodiment of the thermographic layer combination according to the invention, consisting of a temporary auxiliary substrate, a temperature-sensitive liquid crystal layer and an anti-reflection layer.

Figure 1:
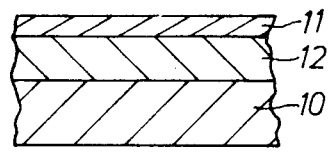

In the production of a thermographic layer combination according to FIG. 1, the temperature-sensitive liquid crystal layer 12 and the anti-reflection layer 11 are applied in that order to the auxiliary substrate 10 by a suitable coating process, for example by brush-coating, spray-coating or casting. It can be seen that the liquid crystal layer is completely embedded between the auxiliary substrate and the anti-reflection layer, so that it is effectively protected against scratching, contamination or destruction, for example under the effect of ultra-violet radiation, during transport, storage or processing of the film system.

Figure 2:
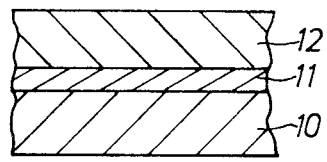

A thermographic layer combination according to FIG. 2 contains the anti-reflection layer 11 and, above it, the temperature-sensitive liquid crystal layer 12 on the temporary substrate layer 10.

Figure 4:
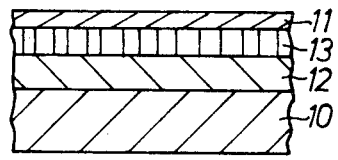
FIG. 4 shows another embodiment of the thermographic layer combination according to the invention with two temperature-sensitive liquid crystal layers one on top of the other.

It can be seen from FIG. 4 that the thermographic layer combination contains two temperature-sensitive liquid crystal layers 12 and 13 between the temporary auxiliary substrate 10 and the anti-reflection layer 11. In this embodiment, too, the liquid crystal layers are largely protected against contamination and mechanical damage. By virtue of a layer combination of the kind shown in FIG. 4, it is possible to cover two different temperature ranges in a single measurement. Similarly, three or more temperature-sensitive liquid crystal layers with different indicating ranges may also be present in the thermographic layer combination according to the invention. The layers 12, 13 can for example be selected so that the indicating range of the one liquid crystal layer 12 begins just where the indicating range of the other liquid crystal layer 13 ends. The advantage of a film system of this kind is that it covers a wider indicating range or, where liquid crystal systems with narrower indicating ranges are used, it is more sensitive to temperature.

Figure 5:
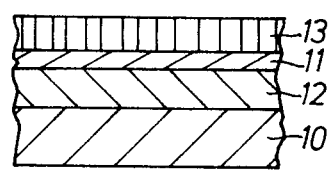
FIG. 5 shows another embodiment of the thermographic layer combination according to the invention with two temperature-sensitive liquid crystal layers on different sides of the anti-reflection layer.

Similarly, a layer combination of the kind shown in FIG. 5 allows measurement to be carried out in either of two temperature ranges. To this end, the thermographic film removed from the auxiliary substrate 10 is placed on the object under examination, on the one hand with the layer 12 and, on the other hand, with the layer 13.

For practical temperature measurement, the thermographic layer combination according to the invention is cut to the required size and applied to a suitable holder, for example to a rigid or elastic frame or to an object to be examined, after which the auxiliary substrate is removed simply by peeling or unrolling it. The auxiliary substrate can also be removed before the film is applied to the object to be measured, the mechanical properties of the film permitting.

In the layer arrangement shown in FIG. 1, the liquid crystal layer is surprisingly left with a high color saturation following removal of the auxiliary substrate, in cases where an auxiliary substrate with a completely smooth surface has been used. This effect is obviously attributable to the completely flat surface of the liquid crystal layer.

It is known that the color of the liquid crystals changes with the angle of incidence of the light. When the surface of liquid crystal layers is uneven, this effect produces an unfavourable reaction insofar as, on the one hand, several colors can be seen at the same temperature and, on the other hand, the purity of the colors is distinctly reduced, as frequently happens in particular in the case of layers with microencapsulated liquid crystals because the capsules project to some extent from the surface of the layer.

This projection of the microcapsules is eliminated by coating a completely smooth auxiliary substrate. In addition, it is possible, especially where the capsules have fairly large diameters, to flatten off the capsules on the surface of the auxiliary substrate as a result of layer shrinkage phenomena during the drying process. The purity of the colors also remains intact where the surface of the auxiliary substrate and, hence, the surface of the liquid crystal layer is given a very fine matt finish, thus eliminating the possibly troublesome reflection of light at the layer surface.

Figure 3:
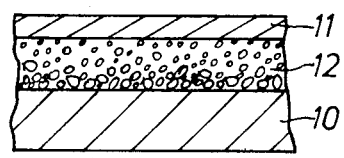

Another advantage of the layer arrangement shown in FIG. 3 and in FIG. 1 is that, where the position of the auxiliary substrate 10 is horizontal, during coating, microencapsulated liquid crystals concentrate at the interface between the temperature-sensitive liquid crystal layer 12 and the auxiliary substrate 10 after coating with the casting solution for the temperature-sensitive layer 12, providing the microcapsules show a tendency towards sedimentation in the casting solution. After the temperature-sensitive layer 12 has been dried, the position of the microcapsules is fixed so that, following removal of the auxiliary substrate 10, there is a high packing density of microcapsules at the surface of the temperature-sensitive layer 12. In addition to the advantages of greater color purity and color density, it has been found that film systems with microcapsules which have sedimented in this way show better mechanical properties in terms of tensile strengths than in cases where the microcapsules are uniformly distributed in the temperature-sensitive layer.

In the method according to the invention, the layer sequence can of course also be such that, as shown in FIG. 2, it is first the anti-reflection layer 11 which is applied to the auxiliary substrate 10, followed by the temperature-sensitive layer 12. This is of advantage especially in cases where the anti-reflection layer 11 which comes into contact with the object under examination is intended to receive a certain type of surface, such as for example a completely smooth surface (good adhesion properties) or a matt surface (no adhesion properties) or even a textured surface, for example in the form of a uniform lattice (point contact with the object under examination).

The temperature-sensitive liquid crystals used for temperature indication in accordance with the invention are cholesteric liquid crystals or solutions of cholesteric liquid crystals, for example in chloroform, or mixtures of different cholesteric liquid crystals or mixtures of cholesteric liquid crystals with nematic liquid crystals or mixtures of nematic liquid crystals with suitable optically active compounds, of the type described for example in Naturwissenschaften 58, 599 (1971). Reference is also made for example to Chemie Ingenieur Technik, 45, 1005 (1973) and Chemiker Zeitung 95, 661 (1971). Provided that suitable substances are selected, it is possible to detect temperature differences of 0.2° K and less.

On account of the sensitivity of the liquid crystals to contamination, they are best used in microencapsulated form. Microencapsulation techniques are adequately known. The microencapsulated liquid crystals are coated with a suitable, preferably water-soluble or water-emulsifiable, binder to form the temperature-sensitive layer.

The anti-reflection layer consists of a binder layer containing a dark, preferably black pigment for example carbon black. Alternatively, the anti-reflection layer can also contain means which, although not initially black enable a black color to be subsequently produced in the anti-reflection layer before the thermographic film is used. When the anti-reflection layer contains for example a photosensitive silver salt such as silver halide, it can be completely or partly blackened as required by uniform exposure or by exposure to a pattern, followed by photographic development. The second of these two procedures makes it possible, for example, to incorporate "windows" in the thermographic film through which the layers lying underneath the anti-reflection layer, for example the layer 12 in FIG. 5 or the object under examination, for example according to FIG. 2, to be observed.

If the auxiliary substrate is to be satisfactorily removed, it must show only limited layer adhesion on its furface in relation to the first layer cast on. The adhesion forces between the auxiliary substrate and the thermographic film must be smaller than those between any two other adjacent layers of the layer composition. On the other hand they must have a minimal value in order to keep together the layer composition until use. Thus it is possible to remove the auxiliary substrate from the thermographic film without destruction of the latter one. Auxiliary substrates whose surface consists, for example, of polyethylene, polytetrafluorethylene, polypropylene, polyester, polycarbonate, polyvinyl chloride, cellulose acetate or acrylic resin, show the required properties.

Either the auxiliary substrate consists throughout of a material with limited layer adhesion properties, such as for example in the case of films, or the auxiliary layer substrate is one with any degree of layer adhesion whose surface has been modified by suitable measures so that it shows the minimal layer adhesion properties required. Examples of auxiliary substrates of this kind include paper or cardboard lined with polyethylene film, or materials coated with solutions of acrylic resins or supporting materials sprayed with a nonstick spray, for example a polytetrafluorethylene spray.

In common with the minimal layer adhesion properties, the auxiliary substrates used for the process according to the invention frequently show poor wetting properties. Accordingly, suitable wetting agents, for example saponin, anionic compounds, for example the alkylaryl sulfonates described in U.S. Pat. No. 2,600,381, amphoteric compounds, of the type described for example in U.S. Pat. No. 3,133,816 or other surface-active agents, are added to the coating suspension to be applied to the auxiliary substrate.

In addition to the functionally necessary constituents, such as the liquid crystal or anti-reflection pigment, the casting solutions required for forming the temperature-sensitive layer combination contain one or more binders through which the required mechanical properties of the film system can be adjusted.

Binders which are soluble or dispersible in water have proved to be particularly suitable for use in the process according to the invention, because on the one hand water as a non-toxic and non-inflammable solvent is ideal for the drying process with problems of pollution control in mind, and because on the other hand the danger of impurities entering the liquid crystal core is considerably reduced.

Suitable binders or constituents of binder mixtures are proteins, for example gelatin or gum arabic, or synthetic compounds such as, for example, polyurethanes, especially those of the kind obtained by reacting polyesters containing hydroxyl groups with polyisocyanates. Particularly suitable binders are, for example, linear polyurethanes of the kind obtained from linear polyesters containing terminal hydroxyl groups by reaction with a diisocyanate, for example hexamethylene diisocyanate, tolylene diisocyanate or 4,4'-bis-phenyl methane diisocyanate, optionally in the presence of dihydroxy, diamino or hydroxyamino compounds acting as bifunctional chain extenders. The polyester used as starting product preferably has an average molecular weight of from 1200 to 3000, and is prepared for example from an aliphatic dicarboxylic acid with 2 to 10 carbon atoms, for example adipic acid, and one or more linear or branched aliphatic dihydroxy compounds with preferably 4 to 8 carbon atoms, such as 1,4-butane diol, 1,6,-hexane diol or neopentyl glycol, the dihydroxy compounds preferably being used in a slight molar excess, based on the dicarboxylic acid. The aforementioned polyurethanes are normally used in the form of aqueous dispersions as binders for the layers of the thermographic film.

In addition, it is possible to use aqueous copolymer dispersions, for example of styrene and butadiene, or mixtures of different copolymer solutions, so that the physical properties such as, for example, tensile strength or elasticity, can be modified in the required manner.

In cases where it is desired to form a film system with favourable elastic properties or high flexural strength, the casting solution containing the liquid crystals can contain additions of the aforementioned binders. After the layer has been dried, the microcapsules containing the liquid crystals can be separated from one another by the binder, the microcapsules being prevented from splitting if the film system is elongated by the elastic properties of the binder.

It has, in practice proved to be particularly suitable to use thermographic films which, following removal of the auxiliary substrate, have a layer thickness of from 10 μm to 100 μm, preferably from 30 to 50 μm, an elasticity modulus of from 0.05 to 1.0 kp/mm² and an elongation at break of more than 5% of their unstretched length.

One particular advantage is the property which a few binders, especially the aforementioned polyurethanes, have of forming elastic films which, even in the event of minimal stressing, undergo temporary plastic deformation, thus further reducing the load on and, hence, the deformation of the object under examination. Another surprising feature of the films is that the plastic deformation of the film in its load-free state is reversible, so that the film assumes its original form within a few seconds to several hours, depending upon the duration and intensity of the load.

By contrast, thermographic films or plates with a supporting film of polyethylene glycol terephthalate show substantially complete inelastic behaviour because the elasticity modulus has a value higher by at least the factor $10^3$.

If, after drying, the layers are to be water-resistant, various organic or inorganic hardeners such as, for example, aldehydes, ketones, sulfonate esters, carboxylic acid derivatives, sulfonyl halides, vinylsulfone ethers, reactive halogen compounds, epoxy compounds, aziridines, reactive olefines, carbodiimides, polymeric hardeners such as, for example, dialdehyde starch and oxyguar rubber, also chrome alum, may be added individually or in combination with one another to the casting solution, especially in the case of natural proteins.

The hardener can of course also be applied by dipping the layer combination into the hardener or a solution of the hardener, or by coating the layer combination with a solution of hardener. Similarly, plasticisers and lubricants, for example polyalcohols, fatty acids, fatty acid esters or silicone resins, may be added to the layers in known manner.

To protect them against external influences, the layers may be provided with thin protective coatings which preferably have little effect upon the overall thickness of the film system. For example, the liquid crystal layer may be covered be a protective layer for ultraviolet light, or alternatively impregnating layers, for example based on silicone, are suitably applied.

We claim:

1. A method of measuring a two-dimensional temperature distribution by means of a thermographic film consisting essentially of a layer containing temperature-sensitive liquid crystals and of an anti-reflection layer, wherein the improvement comprises using a layer combination comprising an auxiliary substrate and arranged thereon, a thermographic film, and removing the auxiliary substrate from the thermographic film before temperature measurement, the thermographic film comprising a layer containing temperature-sensitive liquid crystals and an anti-reflection layer, the thermographic film having an elasticity modulus of 0.05 to 1.0 kp/mm² and an elongation at break of more than 5% of its length when free from load.

2. A method as claimed in claim 1, wherein the layer combination, comprising the auxiliary substrate and thermographic film, is applied to a holder or to an object to be examined before the auxiliary substrate is removed from the thermographic film.

3. A thermographic layer combination which comprises an auxiliary substrate and supported thereon a thermographic film comprising a layer containing temperature-sensitive liquid crystals and an anti-reflection layer, the thermographic film having an elasticity modulus of 0.05 to 1.0 kp/mm² and an elongation at break of more than 5% of its length when free from load, and the layer adhesion forces between the thermographic film and the auxiliary substrate being small enough to enable the auxiliary substrate to be removed from the thermographic film without destruction of the latter.

4. A thermographic layer combination as claimed in claim 3, wherein the liquid crystal layer is arranged between the auxiliary substrate and the anti-reflection layer, and wherein that surface of the auxiliary substrate facing the liquid crystal layer is completely smooth 5. A thermographic layer combination as claimed in claim 3, wherein the anti-reflection layer contains a dispersion of carbon black salt.

6. A thermographic layer combination as claimed in claim 3, wherein the layers of the thermographic film contain a water-soluble binder.

7. A thermographic layer combination as claimed in claim 3, wherein the film contains as a binder a polyurethane obtained from a linear polyester with terminal hydroxyl groups by reaction with a diisocyanate in the presence of bifunctional chain extender.

8. A thermographic layer combination as claimed in claim 3, wherein a thin protective layer is arranged over the liquid crystal layer to protect it from ultraviolet light.

9. A thermographic layer combination as claimed ain claim 3, wherein the thermographic film contains several liquid crystal layers with different indicating ranges.

10. A thermographic layer combination as claimed in claim 3, wherein the liquid crystal layer is arranged between the auxiliary substrate and the anti-reflection layer, and wherein that surface of the auxiliary substrate facing the liquid crystal layer or is matted to a limited extent.

11. A thermographic layer combination as claimed in claim 3, wherein the anti-reflection layer contains a photographically developable silver salt.

12. A thermographic layer combination as claimed in claim 3, wherein the layers of the thermographic film contain a water-dispersible binder.

* * * * *